(12) United States Patent
Miyasa et al.

(10) Patent No.: US 10,068,056 B2
(45) Date of Patent: Sep. 4, 2018

(54) MEDICAL DIAGNOSIS SUPPORT SYSTEM

(75) Inventors: Kazuhiro Miyasa, Yokohama (JP); Yoshio Iizuka, Yokohama (JP); Akihiro Katayama, Yokohama (JP); Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1604 days.

(21) Appl. No.: 12/748,324

(22) Filed: Mar. 26, 2010

(65) Prior Publication Data

US 2010/0256459 A1    Oct. 7, 2010

Related U.S. Application Data

(63) Continuation of application No. PCT/JP2008/067445, filed on Sep. 26, 2008.

(30) Foreign Application Priority Data

Sep. 28, 2007 (JP) .................. 2007-256009

(51) Int. Cl.
*A61B 5/00* (2006.01)
*G06F 19/00* (2018.01)
*G06Q 50/22* (2018.01)

(52) U.S. Cl.
CPC .......... *G06F 19/321* (2013.01); *G06Q 50/22* (2013.01)

(58) Field of Classification Search
CPC ................................................. G06F 19/321

(Continued)

(56) References Cited

U.S. PATENT DOCUMENTS 5,235,510 A * 8/1993 Yamada ................ G06F 19/321
                                                      128/922
5,289,374 A * 2/1994 Doi et al. .................... 600/407

(Continued)

FOREIGN PATENT DOCUMENTS

JP        04-333972 A      11/1992
JP        2004-167087 A    6/2004

(Continued)

OTHER PUBLICATIONS

Office Action dated Feb. 26, 2014, in counterpart European Patent Application No. 08833705.0.

*Primary Examiner* — Gary Jackson
*Assistant Examiner* — Zahed Kabir
(74) *Attorney, Agent, or Firm* — Carter, Deluca, Farrell & Schmidt, LLP

(57) ABSTRACT

This invention provides a mechanism for making a doctor surely follow correct procedures in which the doctor confirms diagnosis information obtained by computer processing after he or she has completed interpretation. A medical diagnosis support apparatus executes diagnosis processing for acquiring medical diagnosis information from an image to be interpreted by computer processing. The medical diagnosis support apparatus accepts interpretation information as an interpretation result of the image to be interpreted, which information is input by, for example, a doctor. The medical diagnosis support apparatus calculates a degree of matching between the diagnosis information and interpretation information, and permits to present the diagnosis information acquired by the diagnosis processing when the calculated degree of matching exceeds a predetermined threshold.

12 Claims, 13 Drawing Sheets

(58) Field of Classification Search
USPC .................................................. 600/300–301
See application file for complete search history.

(56) References Cited

U.S. PATENT DOCUMENTS

| | | | | |
|---|---|---|---|---|
| 5,779,634 | A * | 7/1998 | Ema et al. .................... | 600/407 |
| 5,807,256 | A * | 9/1998 | Taguchi et al. ............... | 600/425 |
| 6,553,356 | B1 * | 4/2003 | Good ..................... | G06F 19/321 |
| | | | | 382/156 |
| 7,244,230 | B2 * | 7/2007 | Duggirala et al. ............ | 600/300 |
| 7,418,121 | B2 * | 8/2008 | Kasai .......................... | 382/128 |
| 7,490,085 | B2 * | 2/2009 | Walker et al. | |
| 7,593,562 | B2 * | 9/2009 | Harrington et al. ......... | 382/141 |
| 7,940,970 | B2 * | 5/2011 | Levanon et al. ............. | 382/128 |
| 8,109,875 | B2 * | 2/2012 | Gizewski ............. | A61B 5/0059 |
| | | | | 600/300 |
| 2002/0188652 | A1 | 12/2002 | Goldhaber et al. | |
| 2004/0100476 | A1 * | 5/2004 | Morita ..................... | G06T 1/00 |
| | | | | 345/619 |
| 2004/0120561 | A1 * | 6/2004 | Goto ................ | 382/128 |
| 2004/0147840 | A1 * | 7/2004 | Duggirala et al. ............ | 600/437 |
| 2005/0002483 | A1 | 1/2005 | Wilcox | |
| 2005/0010445 | A1 * | 1/2005 | Krishnan et al. ................. | 705/2 |
| 2005/0041844 | A1 * | 2/2005 | Yamanaka .................... | 382/128 |
| 2005/0049497 | A1 * | 3/2005 | Krishnan et al. ............. | 600/437 |
| 2006/0050943 | A1 * | 3/2006 | Ozaki et al. .................. | 382/131 |
| 2006/0100507 | A1 * | 5/2006 | Mertelmeier ................. | 600/425 |
| 2006/0122467 | A1 * | 6/2006 | Harrington et al. .......... | 600/300 |
| 2006/0173303 | A1 | 8/2006 | Yu et al. | |
| 2006/0215894 | A1 * | 9/2006 | Lakare .......................... | 382/128 |
| 2007/0274585 | A1 * | 11/2007 | Zhang et al. ................. | 382/132 |
| 2008/0058611 | A1 * | 3/2008 | Tsubura ....................... | 600/300 |
| 2008/0095418 | A1 * | 4/2008 | Moriya ......................... | 382/128 |
| 2008/0118139 | A1 * | 5/2008 | Huo et al. ..................... | 382/132 |
| 2008/0243395 | A1 * | 10/2008 | Oosawa et al. ................. | 702/19 |
| 2008/0294012 | A1 * | 11/2008 | Kurtz et al. .................. | 600/300 |
| 2011/0137132 | A1 * | 6/2011 | Gustafson ............ | A61B 5/4312 |
| | | | | 600/300 |

FOREIGN PATENT DOCUMENTS

| | | |
|---|---|---|
| JP | 2004-261300 A | 9/2004 |
| JP | 2006-115921 A | 5/2006 |
| WO | 2002/09357 A2 | 1/2002 |
| WO | 2007/056601 A2 | 5/2007 |

* cited by examiner

FIG. 10

| TYPE OF FINDING | FINDING INPUT FORMAT | |
|---|---|---|
| | | FINDING ITEM |
| NORMAL FINDING | | REGION CONFIRMED AS NORMAL |
| ABNORMAL FINDING | | REGION OF ABNORMALITY |
| | | CENTRAL POSITION OF ABNORMALITY |
| | | ROI INCLUDING ABNORMALITY |
| | | TYPE OF ABNORMALITY |
| | | DEGREE OF ABNORMALITY (SIZE, ABNORMAL LEVEL, ETC.) |
| | | SUSPECTED DISEASE |

FIG. 11

| TYPE OF FINDING | FINDING ITEM | | SCALE OF DEGREE OF MATCHING |
|---|---|---|---|
| NORMAL FINDING | LOCATION OF FINDING | | 1 IF MATCH, 0 IF DIFFERENT |
| ABNORMAL FINDING | (1) LOCATION OF FINDING | | 1 IF MATCH, 0 IF DIFFERENT |
| | (2) TYPE OF ABNORMALITY | | 1 IF MATCH, 0 IF DIFFERENT |
| | (3) DEGREE OF ABNORMALITY (SIZE, ABNORMAL LEVEL, ETC.) | | EVALUATE BETWEEN 0 TO 1 ACCORDING TO VALUE DIFFERENCE |
| | (4) SUSPECTED DISEASE | | 1 IF MATCH, 0 IF DIFFERENT |

SCALE OF DEGREE OF MATCHING FOR EACH FINDING ITEM

FIG. 12

LIST OF DEGREES OF MEDICAL IMPORTANCE (EXAMPLE)

| ORIGINAL SITE | TYPE OF ABNORMALITY | DEGREE OF ABNORMALITY (SIZE, ABNORMAL LEVEL) | DEGREE OF MEDICAL IMPORTANCE |
|---|---|---|---|
| LUNG | NODULE | 2.0 cm OR MORE | 10 |
| | | 1.5~2.0 cm | 8 |
| | | 1.0~1.5 cm | 6 |
| | | 0.5~1.0 cm | 4 |
| | | 0.5 cm OR LESS | 2 |
| | GGO | 2.0 cm OR MORE | 10 |
| | | 1.5~2.0 cm | 8 |
| | | 1.0~1.5 cm | 6 |
| | | 0.5~1.0 cm | 4 |
| | | 0.5 cm OR LESS | 2 |
| | DIFFUSE SHADE | ABNORMALITY LEVEL 8~10 | 10 |
| | | ABNORMALITY LEVEL 6~8 | 8 |
| | | ABNORMALITY LEVEL 4~6 | 6 |
| | | ABNORMALITY LEVEL 2~4 | 4 |
| | | ABNORMALITY LEVEL 0~2 | 2 |
| ⋮ | ⋮ | ⋮ | ⋮ |

FIG. 13

| | INFORMATION TO BE COMPARED ||
|---|---|---|
| | IMAGE TO BE INTERPRETED | IMAGE OF SIMILAR CASE |
| INTERPRETATION REPORT | α | β |
| CAD DIAGNOSIS INFORMATION | A | B |

MEDICAL DIAGNOSIS SUPPORT SYSTEM

CROSS REFERENCE TO RELATED APPLICATIONS

This application is a CONTINUATION of PCT application No. PCT/JP2008/067445 filed on Sep. 26, 2008 which claims priority from the benefit of Japanese Patent Application No. 2007-256009 filed on Sep. 28, 2007, the disclosures of which are hereby incorporated by reference herein in their entirety.

TECHNICAL FIELD

The present invention relates to a medical diagnosis support system, which applies computer processing to medical image data, and presents obtained diagnosis information.

BACKGROUND ART

In the medical field, a doctor displays medical images obtained by capturing images of a patient on a monitor, interprets the displayed medical images, and observes a state or temporal change of a morbid portion. Apparatuses which generate medical images of this type include:
 CR (Computed Radiography) apparatuses,
 CT (Computed Tomography) apparatuses,
 MRI (Magnetic Resonance Imaging) apparatuses, and
 Ultrasound systems (US).

For the purpose of reducing the interpretation burden placed on doctors, a medical image processing apparatus, which allows a doctor to make a computer-aided diagnosis to automatically detect a morbid portion by converting medical images into digital images and applying image analysis to these images has been developed. The term computer-aided diagnosis will be abbreviated as CAD hereinafter. CAD automatically detects abnormal shade candidates as morbid portions. In this abnormal shade detection processing, computer processing is applied to image data which expresses a radiation image to detect an abnormal mass shade that shows, for example, a cancer, a high-density microcalcification shade, or the like. By presenting this detection result, the interpretation burden placed on the doctor can be reduced, and the interpretation result accuracy can be improved.

Normally, as correct procedures in the use of CAD in an actual clinical site, the doctor first performs interpretation of images, then refers to diagnosis support information output from the CAD system, and compares that information with the interpretation result of himself or herself. More specifically, in this work, the doctor associates pieces of information of findings that has been found, included in an interpretation report written by himself or herself together with the diagnosis support information calculated by the CAD with each other, and uses such information to find oversights, detection errors, differences of findings, and the like. When the doctor interprets after he or she confirms information presented by the CAD without following the procedures, the doctor's resulting interpretation is influenced by the information presented by the CAD. In this way, when the doctor makes a diagnosis depending on the CAD information, if the CAD result includes errors or oversights, the doctor may make an incorrect decision or may not notice oversights.

Therefore, a mechanism whereby the system carries out side checks to confirm that the doctor has completed their interpretation, and presents the CAD result only when it is judged that the interpretation is complete needs to be provided. To meet this demand, patent reference 1 describes a technique which judges that interpretation is complete when the doctor makes an operation to display a screen different from images displayed at the time of interpretation or when a predetermined period of time has elapsed. According to patent reference 1, a mechanism can be provided which automatically judges whether or not interpretation by the doctor is complete, and does not allow the doctor to advance to the next step when it is judged that interpretation is incomplete.

[Patent Reference 1] Japanese Patent Laid-Open No. 2004-167087

DISCLOSURE OF INVENTION

Problems that the Invention is to Solve

However, the technique described in patent reference 1 merely judges completion of interpretation based on a doctor's operation and an elapsed time period. When the doctor really does not interpret images, if the condition of the required operation or elapsed time period is satisfied, it is judged that interpretation is complete. Therefore, in order to assure the doctor practices the correct interpretation procedures, there is a need to decide whether the interpretation is complete based on the contents interpreted by the doctor.

The present invention has been made in consideration of the aforementioned problems, and has as its object to provide a mechanism to increase the liability with which a doctor will follow the correct procedures where the doctor completes interpretation and then confirms the diagnosis by computer processing.

Means of Solving the Problems

In order to achieve the above object, a medial diagnosis support apparatus according to one aspect of the present invention comprises the following arrangement. That is, a medial diagnosis support apparatus comprises:
 diagnosis processing means for acquiring medical diagnosis information from an image to be interpreted by computer processing;
 input means for inputting interpretation information as an interpretation result of the image to be interpreted;
 calculation means for calculating a degree of matching between the diagnosis information and the interpretation information; and
 permission means for, when the degree of matching calculated by the calculation means exceeds a predetermined threshold, permitting to present the diagnosis information acquired by the diagnosis processing means.

In order to achieve the above object, a medial diagnosis support apparatus according to another aspect of the present invention comprises the following arrangement. That is, a medial diagnosis support apparatus comprises:
 storage means for storing previous medical images and pieces of related previous interpretation information;
 diagnosis processing means for acquiring medical diagnosis information from an image to be interpreted by computer processing;
 input means for inputting interpretation information as an interpretation result of the image to be interpreted;
 acquisition means for specifying a previous medical image related to the image to be interpreted from the storage means, and acquiring previous interpretation information corresponding to the specified previous medical image from the storage means;

calculation means for calculating a degree of matching between descriptions included in the previous interpretation information acquired by the acquisition means and the interpretation information input by the input means; and permission means for, when the degree of matching calculated by the calculation means exceeds a predetermined threshold, permitting to present the diagnosis information acquired by the diagnosis processing means.

In order to achieve the above object, a medial diagnosis support apparatus according to another aspect of the present invention comprises the following arrangement. That is, a medical diagnosis support apparatus for acquiring diagnosis information from examination data, comprises:

input means for inputting interpretation information of a doctor; and output means for judging an accuracy of diagnosis information, which is generated based on the interpretation information input by the input means, based on diagnosis information generated from examination data, and outputting the diagnosis information generated from the examination data according to the judgment result.

A method of controlling a medical diagnosis support apparatus according to another aspect of the present invention is a method of controlling a medical diagnosis support apparatus, comprising:

a diagnosis processing step of acquiring medical diagnosis information from an image to be interpreted by computer processing;

an input step of inputting interpretation information as an interpretation result of the image to be interpreted;

a calculation step of calculating a degree of matching between the diagnosis information and the interpretation information; and a permission step of, when the degree of matching calculated in the calculation step exceeds a predetermined threshold, permitting to present the diagnosis information acquired in the diagnosis processing step.

Furthermore, a method of controlling a medical diagnosis support apparatus according to another aspect of the present invention is a method of controlling a medical diagnosis support apparatus, which comprises storage means for storing previous medical images and pieces of related previous interpretation information, comprising:

a diagnosis processing step of acquiring medical diagnosis information from an image to be interpreted by computer processing;

an input step of inputting interpretation information as an interpretation result of the image to be interpreted;

an acquisition step of specifying a previous medical image related to the image to be interpreted from the storage means, and acquiring previous interpretation information corresponding to the specified previous medical image from the storage means;

a calculation step of calculating a degree of matching between descriptions included in the previous interpretation information acquired in the acquisition step and the interpretation information input in the input step; and a permission step of, when the degree of matching calculated in the calculation step exceeds a predetermined threshold, permitting to present the diagnosis information acquired in the diagnosis processing step.

Moreover, a method of controlling a medical diagnosis support apparatus according to another aspect of the present invention is a method of controlling a medical diagnosis support apparatus to acquire diagnosis information from examination data, comprising:

an input step of inputting interpretation information from a doctor; and an output step of judging an accuracy of diagnosis information, which is generated based on the interpretation information input in the input step, based on diagnosis information generated from examination data, and outputting the diagnosis information generated from the examination data according to the judgment result.

Other features and advantages of the present invention will become apparent from the following description taken in conjunction with the accompanying drawings. Note that the same reference numerals denote the same or similar components throughout the accompanying drawings.

Effect of the Invention

The arrangement of the present invention can provide a mechanism to ensure that a doctor follows the correct procedures in interpreting information, and then confirm the diagnosis information through computer processing.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 10 is a view showing an input format for findings in step S203 in FIG. 2 according to the first embodiment;

FIG. 11 is a view showing scales of degrees of matching for respective finding items in step S501 in FIG. 5 according to the second embodiment;

FIG. 12 is a view showing an example of a list of degrees of medical importance in step S503 in FIG. 5 according to the second embodiment; and FIG. 13 is a view showing four pieces of information to be compared in step S907 in FIG. 9 according to the fourth embodiment.

BEST MODE FOR CARRYING OUT THE INVENTION

Preferred embodiments of a medical diagnosis support apparatus and method according to the present invention will be described in detail hereinafter with reference to the accompanying drawings. However, the scope of the invention is not limited to illustrated examples.

First Embodiment

Figure 1:
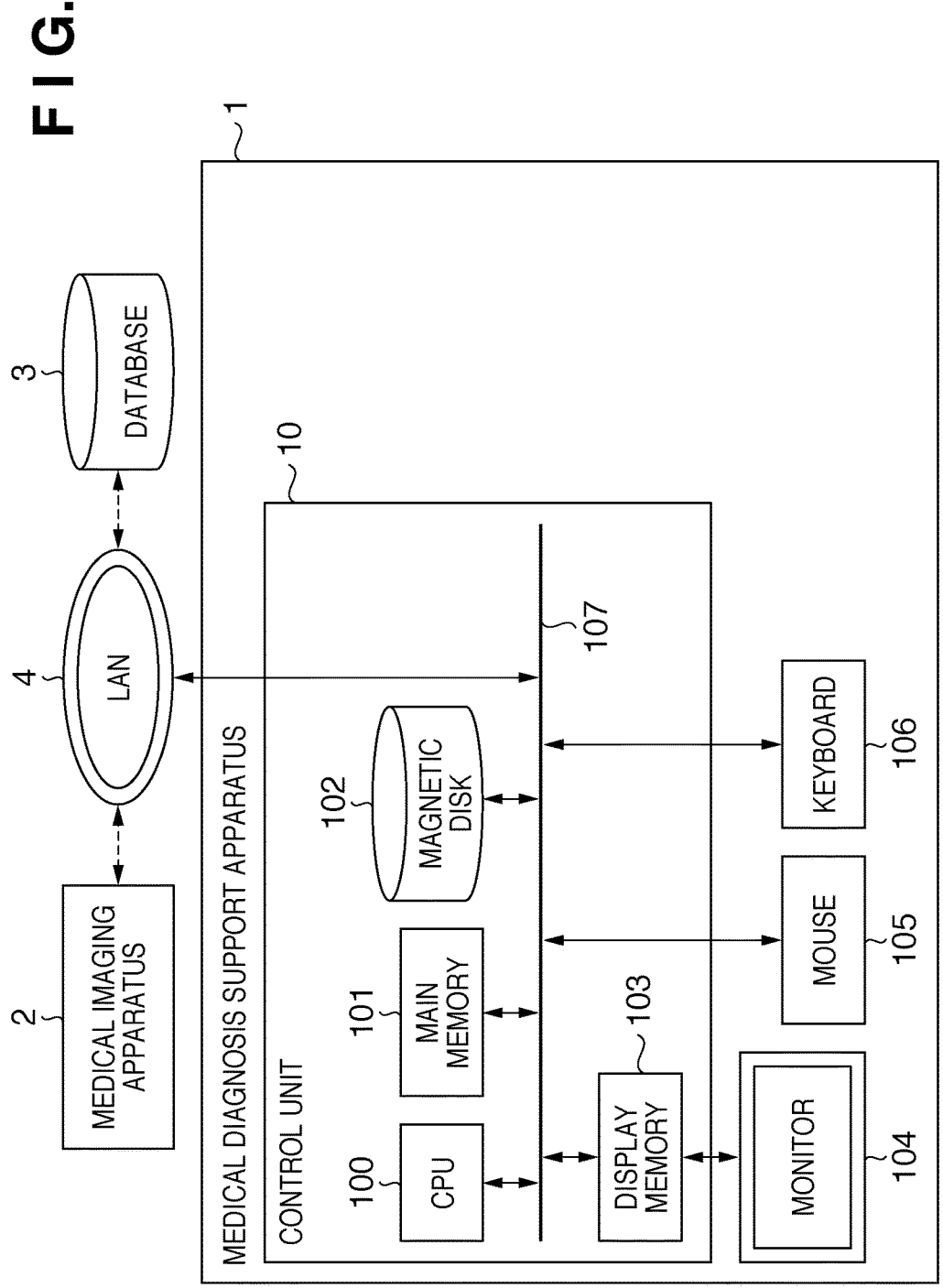
FIG. 1 is a block diagram showing the apparatus arrangement of a medical diagnosis support apparatus 1 according to the first embodiment.

FIG. 1 is a block diagram showing an example of the apparatus arrangement of a medical diagnosis support system according to the first embodiment. Referring to FIG. 1, a medical diagnosis support apparatus 1 has a control unit 10, monitor 104, mouse 105, and keyboard 106. The control unit 10 has a central processing unit (CPU) 100, main memory 101, magnetic disk 102, and display memory 103. Then, when the CPU 100 executes programs stored in the main memory 101, various kinds of control including communications with a medical imaging apparatus 2 and database 3, and the overall control of the medical diagnosis support apparatus 1 are implemented.

As shown in FIG. 1, the medical diagnosis support apparatus 1 is connected to the medical imaging apparatus 2 which can capture images of an object. The medical imaging apparatus 2 includes, for example, an X-ray CT apparatus, MRI apparatus, US apparatus, X-ray apparatus, and nuclear medicine apparatus. The medical diagnosis support apparatus 1 may be connected to the database 3 which stores medical images captured by the medical imaging apparatus 2 and medical examination data including information required for diagnosis support processing, and may acquire required medical images and the like from the database 3.

The CPU 100 mainly controls the operations of the respective components of the medical diagnosis support apparatus 1. The main memory 101 stores control programs to be executed by the CPU 100, and provides a work area when the CPU 100 executes the programs. The magnetic disk 102 stores an operating system (OS), device drivers of peripheral devices, various kinds of application software including programs required to execute diagnosis support processing (to be described later), and the like. The display memory 103 temporarily stores display data for the monitor 104. The monitor 104 includes, for example, a CRT monitor or liquid crystal monitor, and displays an image based on data from the display memory 103. The mouse 105 and keyboard 106 respectively allow the user to make pointing inputs and to input characters and the like. The respective components are connected via a common bus 107 to be able to communicate with each other.

In this embodiment, the medical diagnosis support apparatus 1 can read out medical image data and the like from the database 3 via a LAN 4. Alternatively, storage devices including, for example, an FDD, CD-RW drive, MO drive, and ZIP drive may be connected to the medical diagnosis support apparatus 1, which may load medical image data and the like from these drives. Also, the medical diagnosis support apparatus 1 may directly acquire medical images and the like from the medical imaging apparatus 2 via the LAN 4.

Figure 2:
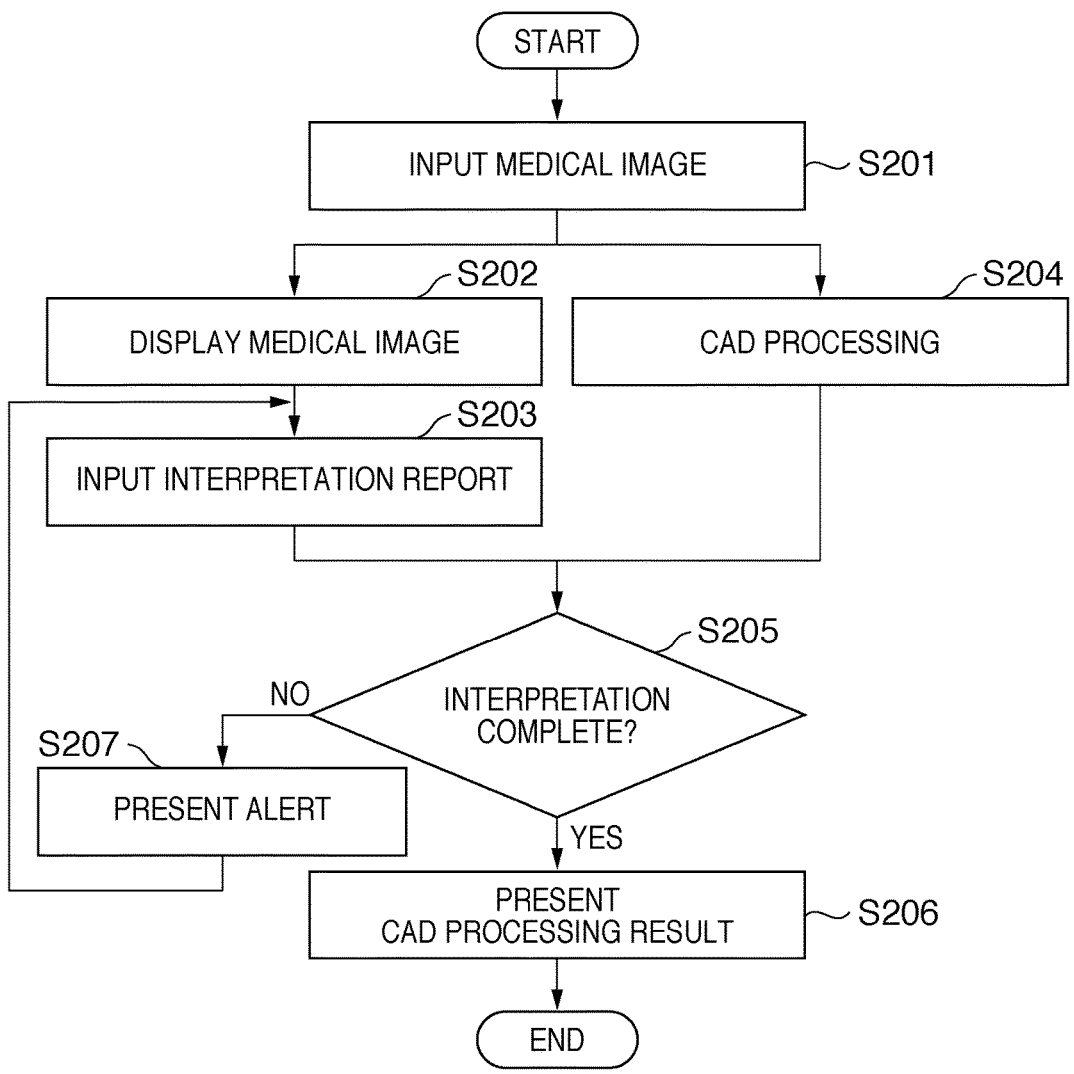
FIG. 2 is a flowchart showing the processing sequence of the medical diagnosis support apparatus 1 according to the first embodiment.

How the control unit 10 controls the medical diagnosis support apparatus 1 will be described below with reference to the flowchart of FIG. 2. Note that the processing shown in the flowchart of FIG. 2 is implemented when the CPU 100 executes programs stored in the main memory 101.

In step S201, the CPU 100 performs processing to input desired medical image data to the medical diagnosis support apparatus 1 in accordance with inputs from the mouse 105 and keyboard 106. The medical image data input in step S201 will be referred to as an image to be interpreted hereinafter. In this image data input processing, for example, the CPU 100 receives, as an image to be interpreted, medical image data from the database 3 that saves captured medical image data via the LAN 4, as described above. Alternatively, the CPU 100 reads, as an image to be interpreted, image data from various storage media of the storage devices, for example, an FDD, CD-RW drive, MO drive, and ZIP drive, which are connected to the medical diagnosis support apparatus 1.

In step S202, the CPU 100 displays the image to be interpreted that was input to the medical diagnosis support apparatus 1 on the monitor 104.

In step S203, the CPU 100 accepts, as an interpretation report, interpretation information created by a doctor as the user, and saves it in, for example, the magnetic disk 102. That is, the interpretation information is input and saved as the doctor's interpretation results for the image to be interpreted that was input in step S201. Note that in this embodiment, a standard format (to be referred to as a finding input format hereinafter) shown in FIG. 10, and choices of contents to be entered in respective items of that format are prepared in advance, and the doctor who made the interpretation selects the choices, thereby generating an interpretation report. In step S203, the CPU 100 presents such finding input format to the doctor and prompts the doctor to select the choices of the respective items, thereby generating an interpretation report.

In step S204, the CPU 100 executes diagnosis processing to obtain medical diagnosis information through computer processing of the image to be interpreted input in step S201. More specifically, the CPU 100 executes processing to apply computer-aided diagnosis (CAD) to the image to be interpreted that was input to the medical diagnosis support apparatus 1, and acquires diagnosis information (to be referred to as diagnosis information acquisition processing hereinafter). During the diagnosis information acquisition process, the CPU 100 executes image processing to detect morbid candidates based on image features in the image to be interpreted first. Next, the CPU 100 executes discrimination to discriminate the authenticity and morbid type of each detected morbid candidate, and generates diagnosis information for medical examination data based on that result. Furthermore, the CPU 100 converts the generated diagnosis information into a format equivalent to the format shown in FIG. 10, that is, the finding input format used in step S203.

The CPU 100 judges in step S205 based on the interpretation report obtained in step S203 and the CAD diagnosis information obtained in step S204 whether or not the doctor wrote the interpretation report after completion of the interpretation, in consideration of the interpretation contents. In this embodiment, the CPU 100 calculates a degree of matching between the diagnosis information obtained by the computer processing and the interpretation information input by the doctor, and judges whether or not the interpretation is complete based on the calculated degree of matching. If it is judged that the interpretation is complete, the process advances to step S206; otherwise, the process advances to step S207.

In association with this decision, since the CAD processing performs abnormality detection and discrimination of the entire image to be interpreted unless an operation error occurs in the middle of the processing, the interpretation is considered to be complete. Therefore, this embodiment uses the CAD diagnosis information as information for judging the contents of the interpretation report (as to whether or not the interpretation is complete).

In this embodiment, as a method of judging the contents of the interpretation report based on the CAD diagnosis information, findings included in them are compared, and when the contents of the interpretation report satisfies given criteria with respect to the CAD diagnosis information, completion of the interpretation is judged.

There are some methods of deciding contents to be compared and given criteria. In this case, whether or not the interpretation is complete is judged from two aspects, that is, quantitative and qualitative aspects associated with the contents of the interpretation report.

Since the CAD diagnosis information is obtained after completing the interpretation, when the number of findings written in the interpretation report is close to that included in the CAD diagnosis information, it can be grounds for judging that the interpretation was carried out thoroughly. Therefore, the numbers of findings included in the interpretation information and diagnosis information are defined as a quantitative aspect, and the result of comparing is used to judge completion of the interpretation.

When the CAD diagnosis information includes findings to be detected/discriminated at the time of interpretation, if the interpretation report created by the doctor includes them, it can be grounds for judging that the contents of the image to be interpreted have been confirmed. Therefore, the number of findings to be detected/discriminated, which are included in the interpretation report, based on the CAD diagnosis information is defined as a qualitative aspect. Note that this embodiment uses the number of "findings which are easily detected/discriminated in this embodiment" as the number of "findings to be detected/discriminated at the time of interpretation". That is, the CPU 100 determines the degree of ease of detection for each findings included in the diagnosis information based on the description of that finding, and uses the result of comparing the numbers of findings included in the interpretation information and diagnosis information in association with findings which have a degree of ease in detection that is larger than a predetermined value.

Figure 3:
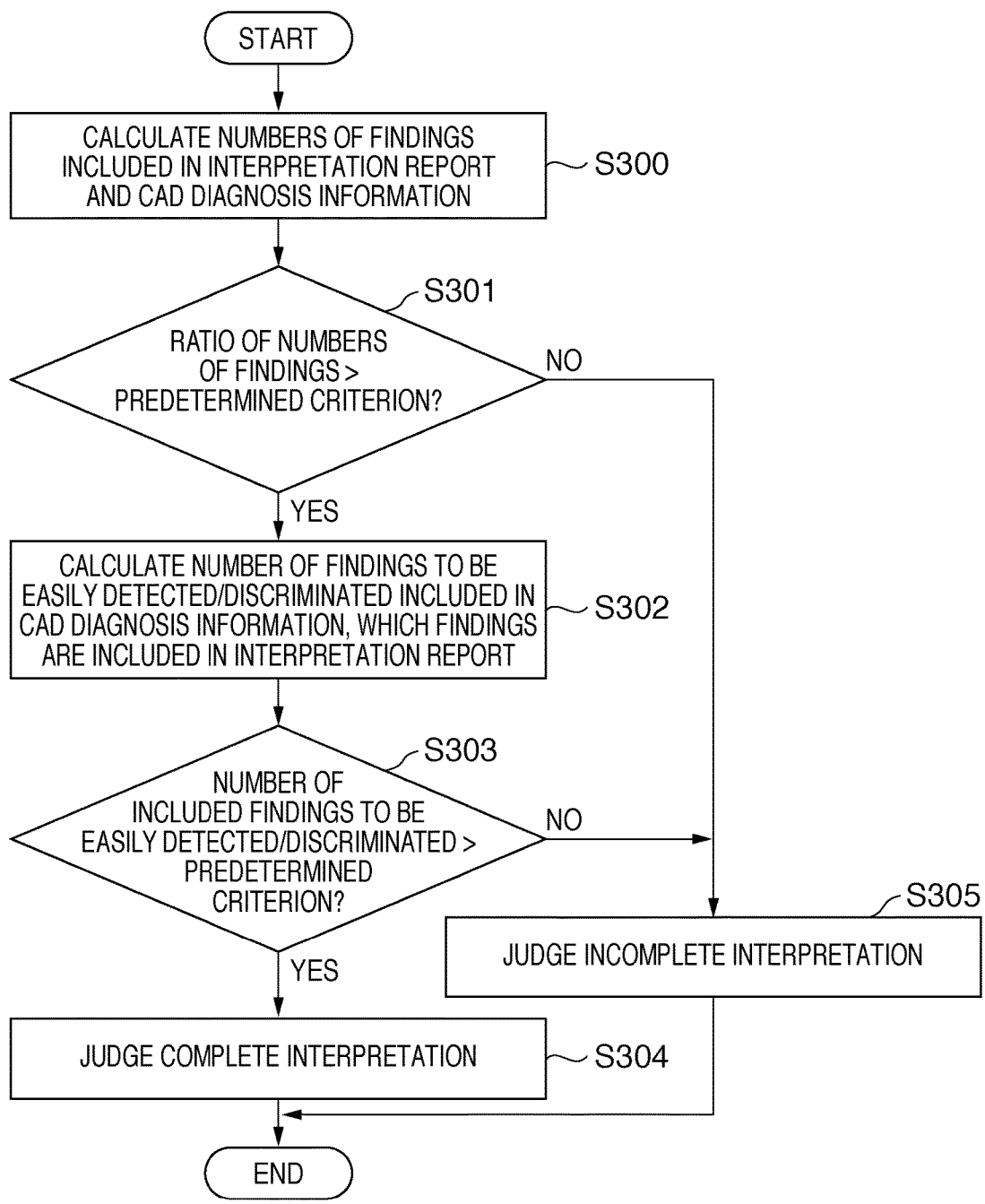
FIG. 3 is a flowchart showing the processing sequence in step S205 in FIG. 2 according to the first embodiment.

FIG. 3 is a flowchart showing an example of discrimination in consideration of the aforementioned two aspects.

In step S300, the CPU 100 calculates the numbers of findings included in the interpretation report and CAD diagnosis information as $N_{REP}$ and $N_{CAD}$, respectively.

The CPU 100 determines in step S301 whether or not a ratio $N_{REP}/N_{CAD}$ of the number of findings in the interpretation report based on that in the CAD diagnosis information is larger than a given value (ratio) $r_1$. If $N_{REP}/N_{CAD} > r_1$, the process advances to step S302; otherwise, the process jumps to step S305. In this embodiment, for example, $r_1 = 0.5$ is set in consideration that the CAD diagnosis information includes false positives.

In step S302, the CPU 100 calculates a general degree of ease of detection/discrimination for each of the findings included in the CAD diagnosis information. For example, when the CAD diagnosis information includes a finding including a finding location: "left lung field" and a type of abnormality: "solitary nodule shade", both the CAD and doctor can detect more easily with increasing size of an abnormal portion indicating a degree of abnormality. Therefore, as a degree of ease of detection/discrimination associated with "solitary nodule shade", a value according to its size is set. For example, values ranging from 0 to 10 are given: "2" when the size ranges from "0 to 0.5 cm"; "4" when it ranges from "0.5 to 1.0 cm"; "6" when it ranges from "1.0 to 1.5 cm"; "8" when it ranges from "1.5 to 2.0 cm"; and "10" when it is "2.0 cm or more". Next, findings that are judged to have high degrees of easiness of detection/discrimination calculated in this way are selected from the CAD diagnosis information. As a selection method, a method of selecting the specific number of findings in descending order of value, a method of selecting all findings having a specific value or more, and the like may be used. This embodiment uses the latter method. For example, findings having values "5" or more as an intermediate value are selected (in case of the solitary nodule, the size is 1.0 cm or more): this number of findings is defined as $N_{D \cdot CAD}$. Furthermore, of the $N_{D \cdot CAD}$ findings that are counted the number of findings that are included in the interpretation report, are defined as $N_{D \cdot C\&R}$.

The CPU 100 determines in step S303 if a ratio $N_{D \cdot C\&R}/N_{D \cdot CAD}$ included in the interpretation report of findings which are included in the CAD and are easily detected/discriminated is larger than a given value (ratio) $r_2$. If $N_{D \cdot C\&R}/N_{D \cdot CAD} > r_2$, the process advances to step S304; otherwise, the process advances to step S305. In this case, for example, assume that $r_2 = 0.7$ is set.

Step S304 is a process executed when $N_{REP}/N_{CAD} > r_1$ and $N_{D \cdot C\&R}/N_{D \cdot CAD} > r_2$, and the CPU 100 performs processing for judging that the doctor has completed the interpretation. On the other hand, step S305 is a process executed when $N_{REP}/N_{CAD} \leq r_1$ or $N_{D \cdot C\&R}/N_{D \cdot CAD} \leq r_2$, and the CPU 100 determines that the doctor has not completed the interpretation. In this embodiment, whether or not the interpretation is complete is determined by the aforementioned method.

As described above, when the calculated degrees of matching ($N_{REP}/N_{CAD}$, $N_{D \cdot C\&R}/N_{D \cdot CAD}$) exceed predetermined thresholds ($r_1$, $r_2$), presentation of the diagnosis information acquired by the diagnosis processing of, for example, the CAD is permitted. In this embodiment, the CPU 100 presents the CAD diagnosis information obtained in step S204 on the monitor in step S206, and the process advances to the end of processing. Of course, presentation of the diagnosis information need not be promptly executed, and may be displayed on, for example, the monitor 104 according to instructions from the doctor.

In step S207, the CPU 100 presents an alert indicating that the interpretation is incomplete and re-interpretation is required, and the process returns to the interpretation report input processing in step S203. Note that the alert can be presented through a method where a popup display is created on the screen, or a method where an audible alert sound or message is generated.

According to the aforementioned arrangement, the following effects can be obtained.

(1) The contents of the CAD diagnosis information and the interpretation report described by the doctor are compared in terms of the quantitative and qualitative aspects to judge whether or not the interpretation is complete. Hence, the judgment based on the interpretation contents can be attained, thus making the doctor follow the correct procedures of the interpretation more reliably.

(2) In particular, by considering how many findings which are included in the CAD diagnosis information and are easily detected/discriminated the interpretation report includes, when medical image data includes findings to be detected/discriminated by necessity, the doctor can be prevented from advancing to the next process without interpreting them.

Modification of First Embodiment

The medical image data input process in step S201 may adopt, for example, the following mode. That is, the medical diagnosis support apparatus 1 is configured to be connected to medial imaging apparatuses that can capture images of an object, such as an X-ray CT apparatus, MR apparatus, US apparatus, X-ray apparatus, and nuclear medicine apparatus, and the CPU 100 directly inputs image data from these apparatuses in step S201.

Step S201 is not limited to the input process of medical image data, but medical examination data including the interpretation report and information required for the diagnosis support processing may be input. In this case, the apparatus may be configured to allow the user to directly input these data, or to read these data from various storage media of an FDD, CD-RW drive, MO drive, and ZIP drive which record information. Or the apparatus may be configured to connect a database that records these data via the LAN and to receive them.

The interpretation report input process in step S203 may adopt the following mode. That is, the apparatus may be configured to allow the doctor who has done the interpretation to directly input the interpretation result information to a computer using the keyboard and mouse. Or by connecting a sheet face reading device such as a paper scanner and OCR (Optical Character Recognition), a hand-written document of the doctor who has done the interpretation may be read in a format that can be edited by a computer. In case of this arrangement, the apparatus requires an arrangement that converts the contents of the input interpretation report into the format shown in FIG. 10 by interpreting medical meanings by natural language processing.

The diagnosis information generation process by means of the CAD processing in step S204 may adopt the following mode. That is, an object to be processed is not limited to medical image data. For example, medical examination data including previous interpretation reports and medical charts associated with an object, and other kinds of information that can be used in diagnosis support processing may be used as objects to be processed. In this case, diagnosis information can be generated based on medical examination data other than image information of an object.

Second Embodiment

The second embodiment will be described below. Note that since the second embodiment adopts the same arrangement as that of the first embodiment, the block diagram of FIG. 1 is used, and a description thereof will not be repeated.

Figure 4:
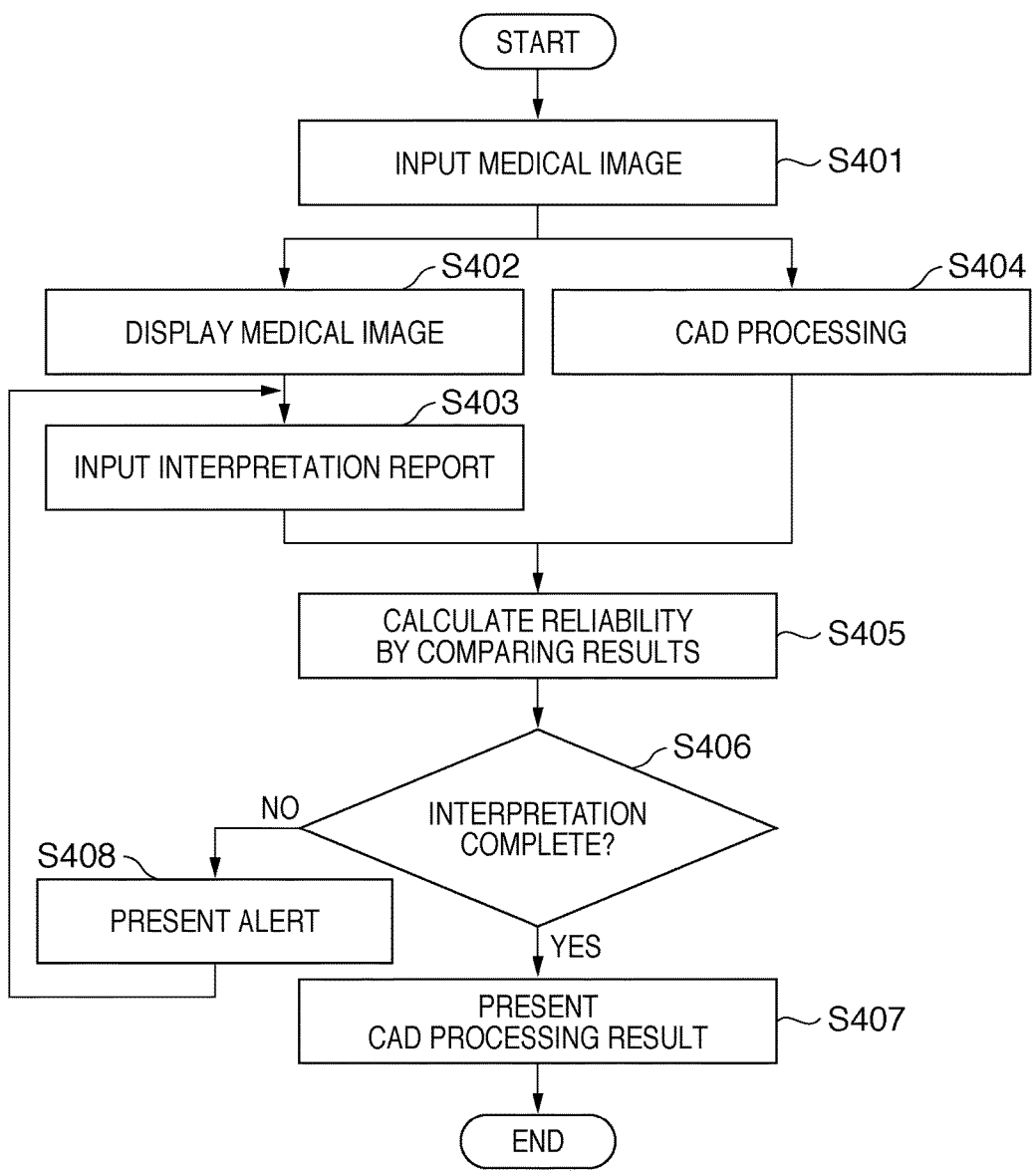
FIG. 4 is a flowchart showing the processing sequence of a medical diagnosis support apparatus 1 according to the second embodiment.

How a control unit 10 controls a medical diagnosis support apparatus 1 will be described below with reference to the flowchart of FIG. 4.

In step S401, a CPU 100 performs processing to input desired medical image data to the medical diagnosis support apparatus 1 in accordance with inputs from a mouse 105 and keyboard 106 (the input medical image data will be referred to as an image to be interpreted hereinafter). In step S402, the CPU 100 performs processing for displaying the image to be interpreted input to the medical diagnosis support apparatus 1 on a monitor 104.

In step S403, the CPU 100 accepts, as an interpretation report, interpretation information input by a doctor to the medical diagnosis support apparatus 1. That is, the interpretation information as the interpretation result of the image to be interpreted is input.

Next, the CPU 100 acquires medical diagnosis information from the image to be interpreted by computer processing. In this embodiment, in step S404, the CPU 100 executes processing for applying CAD processing to the image to be interpreted input to the medical diagnosis support apparatus 1, and acquiring diagnosis information.

The CPU 100 then calculates a degree of matching between the diagnosis information acquired in step S404 and the interpretation information input in step S403. In this embodiment, in step S405, the CPU 100 compares the interpretation report obtained in step S403 and the CAD diagnosis information obtained in step S404, and calculates a reliability of the interpretation report based on the CAD diagnosis information. This reliability is used to judge whether or not the doctor has completed interpretation in consideration of the interpretation contents. That is, the degree of matching between the diagnosis information and the interpretation information corresponds to the reliability of the interpretation information. In the second embodiment, when this reliability is high, it is judged that the interpretation information is created after completion of the interpretation.

Upon comparison between the interpretation report and the diagnosis information, when the CAD diagnosis information includes medically important findings, if the interpretation report fully covers these findings, the reliability upon judging completion of the interpretation is high. Hence, the second embodiment calculates how many findings having higher degrees of medical importance included in the CAD diagnosis information the interpretation report can detect, and defines it as the reliability of the interpretation report. A method of practically calculating the reliability of the interpretation report by comparing the interpretation report and diagnosis information will be described later.

The CPU 100 judges in step S406 whether or not the interpreting doctor has completed the interpretation by seeing if the reliability of the interpretation report obtained in step S405 satisfies a given criterion. If completion of the interpretation is judged, the process advances to step S407; otherwise, the process advances to step S408. A practical reliability criterion determination method will be described later.

As described above, when the calculated reliability (degree of matching) exceeds a predetermined threshold, the CPU 100 permits presentation of the diagnosis information acquired through the diagnosis processing in step S404. In this embodiment, in step S407, the CPU 100 presents the CAD diagnosis information obtained in step S404 on the monitor, and the process then advances to the end of processing. On the other hand, in step S408, the CPU 100 presents an alert indicating that the interpretation is incomplete and re-interpretation is required, and the process returns to the interpretation report input processing in step S403. Note that the alert can be presented by a method of making a popup display on the screen, or a method of generating an audible alert sound or message.

The processes in steps S405 and S406 will be practically described below.

The method of calculating the reliability of the interpretation report by comparing the interpretation report and the CAD diagnosis information in step S405 will be practically described first.

Figure 5:
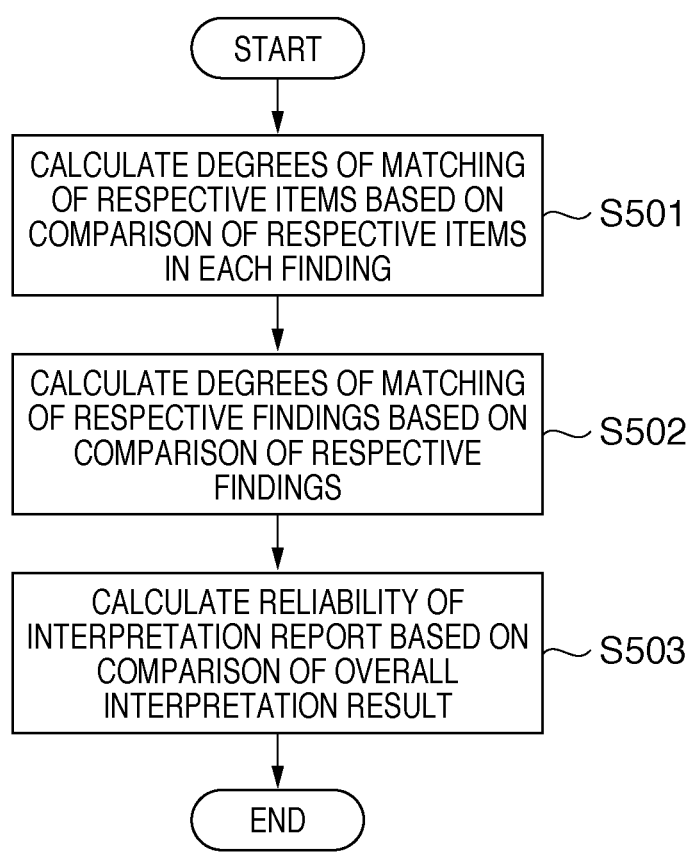
FIG. 5 is a flowchart showing the processing sequence in step S405 in FIG. 4 according to the second embodiment.

FIG. 5 is a flowchart showing the sequence for comparing the interpretation report and CAD diagnosis information.

First, the degree of matching is calculated for each finding item included in the interpretation information and diagnosis information. In this embodiment, in step S501, the CPU 100 compares respective predetermined items set in each finding in association with the interpretation report and CAD diagnosis information, and calculates degree of matching for each of the items (to be referred to as degrees of matching associated with respective items) using predetermined scales. FIG. 11 shows scales required to calculate the degrees of matching for respective items in a finding.

In comparison of item units shown in FIG. 11, as for a normal finding, an item to be compared includes only the location of a finding. On the other hand, an abnormal finding includes a plurality of items to be compared, and there are items that cannot be compared unless specific items match as follows.

First, comparison of a type of abnormality between two findings is premised on that locations of abnormality match.

Second, comparison of a degree of abnormality between two findings is premised on that the types of abnormality match.

Third, comparison of a suspected disease between two findings is premised on that the types of abnormality match.

Therefore, comparison of the abnormal finding is made in a stepwise fashion in turn from items premised on their matches required to compare other items.

Figure 6:
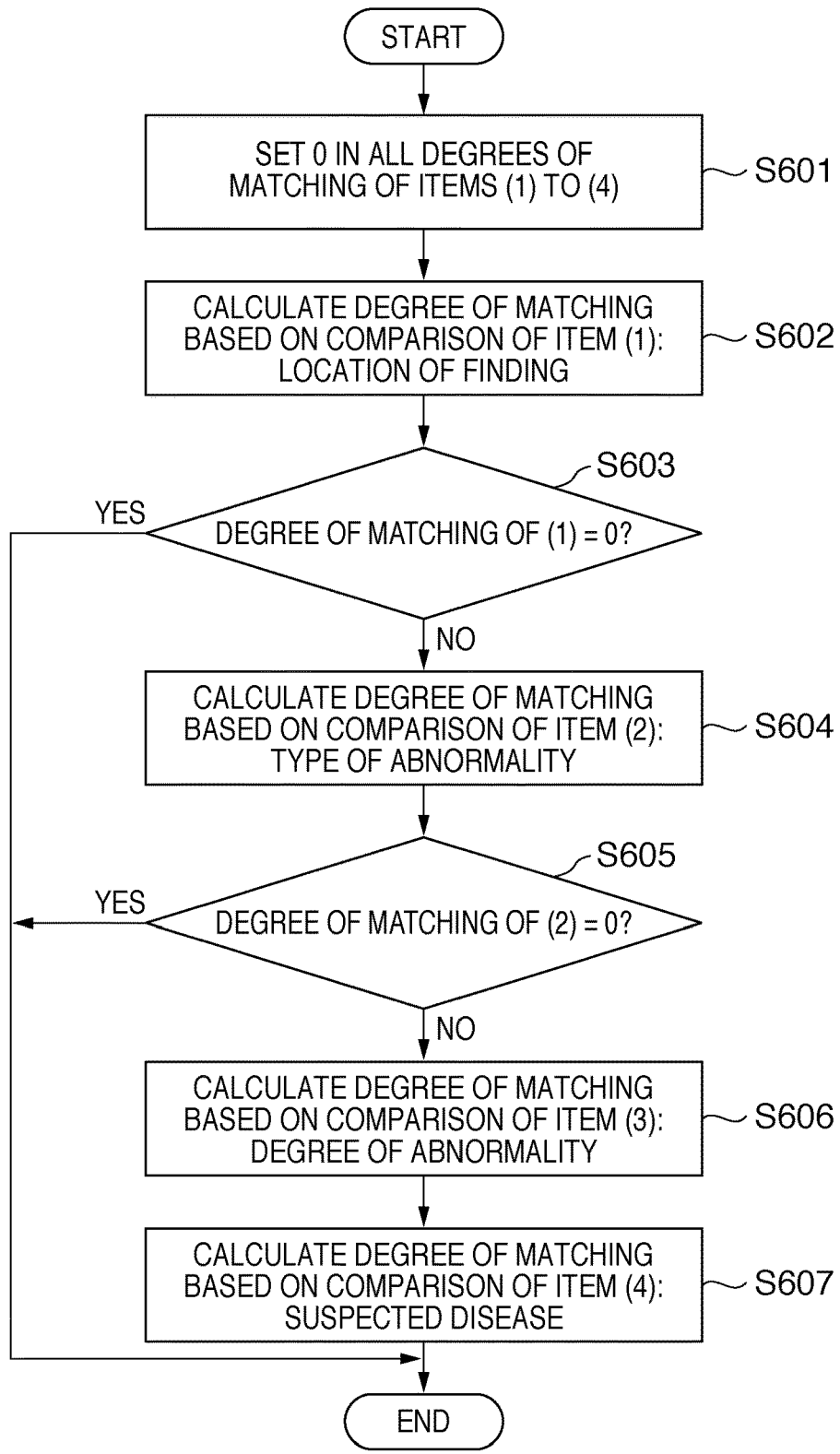
FIG. 6 is a flowchart showing the processing sequence in step S501 in FIG. 5 according to the second embodiment.

FIG. 6 shows the sequence for comparing respective items shown in FIG. 11 in turn to calculate degrees of matching.

In step S601, the CPU 100 performs processing for setting zero in all degrees of matching of items (1) to (4) in FIG. 11 first.

In step S602, the CPU 100 compares an item "(1): location of finding" in FIG. 11. A degree of matching of the location of the finding is defined by $c_1$, and if it is determined that findings have the same location, $c_1=1$ is set; if it is determined that the findings have different locations, $c_1=0$ is set.

If the CPU 100 determines in step S603 that the findings have the same location ($c_1=1$) in step S602, the process advances to step S604; if it judges that the findings have different locations ($c_1=0$), this processing ends.

In step S604, the CPU 100 compares an item "(2): type of abnormality" for the findings having the same location. A degree of matching of the type of abnormality is defined by $c_2$, and if the types match, $c_2=1$ is set; if the types are different, $c_2=0$ is set.

If the CPU 100 determines in step S605 that the types of abnormality match ($c_2=1$) in step S604, the process advances to step S606; if it determines that the types do not match ($c_2=0$), this processing ends.

In step S606, the CPU 100 compares "(3): degree of abnormality" for the findings whose types of abnormality match. A degree of matching of a degree of abnormality is defined by $c_3$, and a value of the degree of matching is given between 0 to 1 according to a difference between the two abnormality levels (sizes of abnormalities). In step S607, the CPU 100 compares suspected diseases for the findings whose types of abnormality match. A degree of matching of a suspected disease is defined by $c_4$, and a value of the degree of matching is given between 0 and 1 according to a difference between the diseases described in the finding items. Note that the values of the degrees of matching according to the differences between diseases may be held in, for example, a table.

With the aforementioned method, the degrees of matching for respective items in each finding are calculated.

Degrees of matching for respective findings included in the interpretation information and diagnosis information are calculated based on the aforementioned degrees of matching for respective finding items. In this embodiment, in step S502, the CPU 100 compares the interpretation report and CAD diagnosis information for respective findings based on the calculation results in step S501, thereby calculating the degrees of matching of the findings.

Upon comparison between findings, a degree of matching of the finding itself is higher as the number of matches between items in each finding calculated in step S501 is larger. Hence, the degree of matching of each finding is defined by C, and is expressed by an weighted average value of the degrees of matching of all the items:

[Mathematical 1]

$$C = \frac{k_1 \cdot c_1 + k_2 \cdot c_2 + k_3 \cdot c_3 + k_4 \cdot c_4}{4} \quad (1)$$
$$(\text{for } k_1 + k_2 + k_3 + k_4 = 4)$$

For example, assume that all the items have the same weight, that is, $k_1=k_2=k_3=k_4=1$.

The degree of matching C of each finding is respectively given to findings to be compared in the interpretation report and the CAD diagnosis information. Degrees of matching $C_i$ and $C_j$ upon comparison between a certain finding i included in the CAD diagnosis information and a certain finding j included in the interpretation report is expressed by $C=C_i=C_j$.

Finally, a total degree of matching (i.e., reliability) between the interpretation information and diagnosis information is calculated based on the degrees of matching for respective findings, which are calculated as described above. In this embodiment, in step S503, the CPU 100 performs overall comparison between the interpretation report and the CAD diagnosis information to calculate a final reliability based on the result in step S502.

The second embodiment defines "how many findings having higher degrees of medical importance included in the CAD diagnosis information the interpretation report can detect" as a reliability.

FIG. 12 shows an example of a list of degrees of medical importance, which are ranked with respect to various findings found by the interpretation. Assume that the degrees of importance are ranked in advance according to the relationship among the respective types of findings with respect to continuation of the life of an object.

Based on FIG. 12, a degree of importance $S_{CADi}$ of a finding i included in the CAD diagnosis information is calculated. Letting $N_{CAD}$ be the total number of findings and i (i=1, 2, . . . , $N_{CAD}$) be each finding number in the CAD diagnosis information, a degree of importance corresponding to a finding i is expressed by $S_{CADi}$.

Likewise, letting $N_{REP}$ be the total number of findings and j (j=1, 2, . . . , $N_{REP}$) be each finding number in the interpretation report, a degree of importance corresponding to a finding j is expressed by $S_{REPj}$. Furthermore, let $C_j$ be a degree of matching of the finding j in the interpretation report.

At this time, the high degree of importance $S_{REPj}$ and high degree of matching $C_j$ for a certain finding j means that the interpretation report can more accurately detect a finding having a high degree of importance included in the CAD diagnosis information. Therefore, if the product of $S_{REPj}$ and $C_j$ is large, the finding j has a high reliability.

This value is calculated for all findings included in the interpretation report, and a value obtained by normalizing the calculated values by dividing them by a total value of the degrees of importance of all the findings included in the CAD diagnosis information is defined as a reliability R of the interpretation report.

That is, the reliability R as the total degree of matching is obtained by calculating, as a degree of matching, a ratio between a value obtained by summing up the products of the degrees of matching (C) and degrees of importance ($S_{REPj}$) for all findings included in the interpretation information and the sum value of the degrees of importance of all findings included in the diagnosis information. As described above, the degree of importance ($S_{REPj}$) is decided based on the contents of finding items included in that finding. Therefore, the reliability R of the second embodiment is expressed by:

[Mathematical 2]

$$R = \frac{\sum_{j=1}^{N_{REP}} C_j \cdot S_{REPj}}{\sum_{i=1}^{N_{CAD}} S_{CADi}} (0 \leq R \leq 1) \quad (2)$$

In the above equation, R=1 when the interpretation report includes findings which perfectly match all the findings included in the CAD diagnosis information. Conversely, R=0 when findings included in the interpretation report are completely different from all the findings included in the CAD diagnosis information. With the aforementioned method, the reliability of the interpretation report is calculated.

The method of setting the criterion of the reliability of the interpretation report in step S406 will be practically described below. Whether or not the interpretation is complete is judged by seeing if the value of the reliability R of the interpretation report exceeds a predetermined value (to be defined as a threshold $R_{th}$ hereinafter).

When the doctor creates an interpretation report, if an image to be interpreted includes findings having high degrees of medical importance, he or she has to find them out by necessity. When the reliability R assumes a low value, this means that the doctor has failed to detect findings having high degrees of medical importance, which are actually included in the image to be interpreted. For this reason, in order to judge completion of the interpretation, the reliability R has to assume a high value.

However, CAD diagnosis information generally includes more false positives than the interpretation result of the interpretation doctor. For this reason, even in the interpretation report, completion of interpretation of which has been confirmed, it is hard to consider that findings that perfectly match all the findings in the CAD diagnosis information are detected. Such findings of false positives included in only the CAD diagnosis method do not often exhibit obvious abnormalities. Therefore, these findings may be set as those having low degrees of medical importance in the CAD diagnosis information. However, a large number of such findings lead to a reliability drop. Therefore, in this embodiment, the threshold $R_{th}$ of the reliability R is set to be 0.8 in consideration of the aforementioned contents.

According to the aforementioned arrangement, the following effects can be obtained.

That is, whether or not the interpretation is complete is judged based on scales as to whether or not the doctor has found important findings to be described in the interpretation report. Then, the judgment based on the interpretation contents can be attained, thus making the doctor follow the correct procedures of the interpretation more reliably.

Especially, in the second embodiment, a situation in which although there are findings having higher degrees of medical importance, the doctor confirms the CAD diagnosis information without interpreting them can be avoided.

Modification of Second Embodiment

Comparison between the interpretation report and the CAD diagnosis information in step S405 may adopt the following mode.

In comparing the interpretation report and the CAD diagnosis information in step S405, an equation for calculating the reliability R may simply calculate a degree that findings included in the interpretation match all the findings included in the CAD diagnosis information (degree of matching). That is, as a total degree of matching, a value obtained by dividing the sum values of the degrees of matching ($C_j$) for all the findings included in the interpretation report by the total number of findings included in the diagnosis information may be used as the reliability R. The reliability R in this case is expressed by:

[Mathematical 3]

$$R = \frac{\sum_{j=1}^{N_{REP}} C_j}{\sum_{i=1}^{N_{CAD}} 1} = \left(\frac{\sum_{j=1}^{N_{REP}} C_j}{N_{CAD}}\right)(0 \leq R \leq 1) \quad (3)$$

In this case, whether or not the interpretation is complete is judged in step S405 by merely seeing if the contents of the two pieces of information match. In order to obtain a high reliability value, even findings having low degrees of importance have to match between the two pieces of information irrespective of degrees of medical importance. For this reason, the threshold $R_{th}$ required to judge completion of the interpretation has to be set to be low.

In consideration of the aforementioned contents, for example, the threshold $R_{th}$ is set to be 0.3 in this embodiment. At this time, by setting a state in which the diagnosis information includes nearly no false positives by enhancing the Specificity performance of the CAD, the contents of the CAD diagnosis information may match more contents of the original interpretation report, completion of the interpretation of which has been confirmed. Therefore, using the CAD diagnosis information after this processing as information to be compared with the interpretation report, a more accurate reliability can be given. The processing for enhancing the Specificity performance of the CAD can be implemented by setting strict criteria of feature amounts required to determine an abnormality (or disease) in processing for determining the authenticities of disease candidates after the disease candidates are detected.

Third Embodiment

Figure 7:
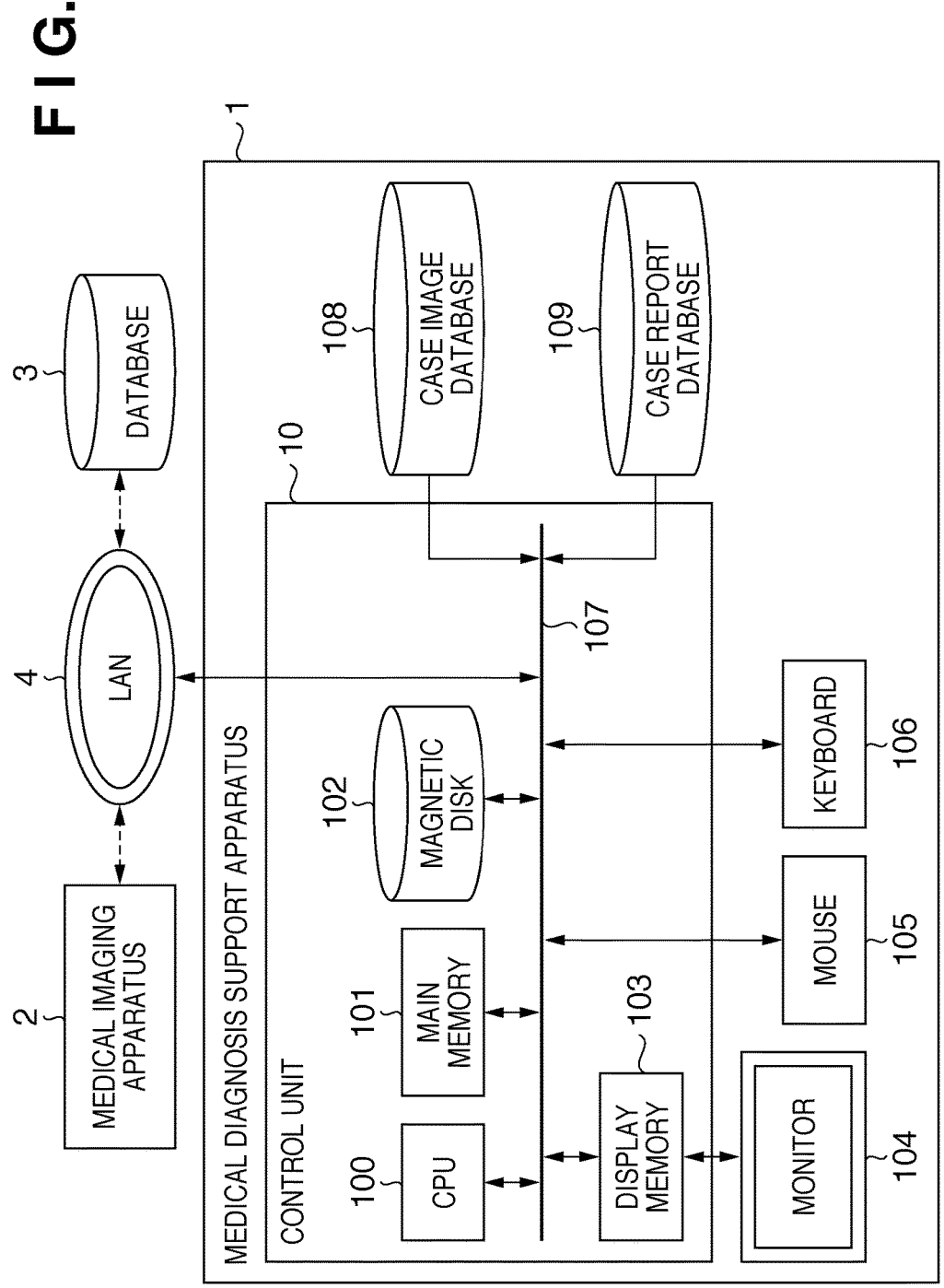
FIG. 7 is a block diagram showing the apparatus arrangement of a medical diagnosis support apparatus 1 according to the third embodiment.

The third embodiment will be described below. The arrangement of a medical diagnosis support apparatus 1 according to the third embodiment will be described first. FIG. 7 is a block diagram showing the apparatus arrangement of the medical diagnosis support apparatus 1 according to the third embodiment. A description about components common to those in the arrangement shown in FIG. 1 in the first embodiment will not be repeated, and only different components will be explained.

The medical diagnosis support apparatus 1 of this embodiment includes a case image database 108 and case report database 109 as a storage unit which stores previous medical images and pieces of their related previous interpretation information. The case image database 108 stores medical images, diagnosis of which is complete. A control unit 10 can read out desired previous case images from the case image database 108 as needed. The case report database 109 stores interpretation reports associated with medical images, diagnosis of which is complete. The control unit 10 can read out desired previous interpretation reports from the case report database 109 as needed.

Figure 8:
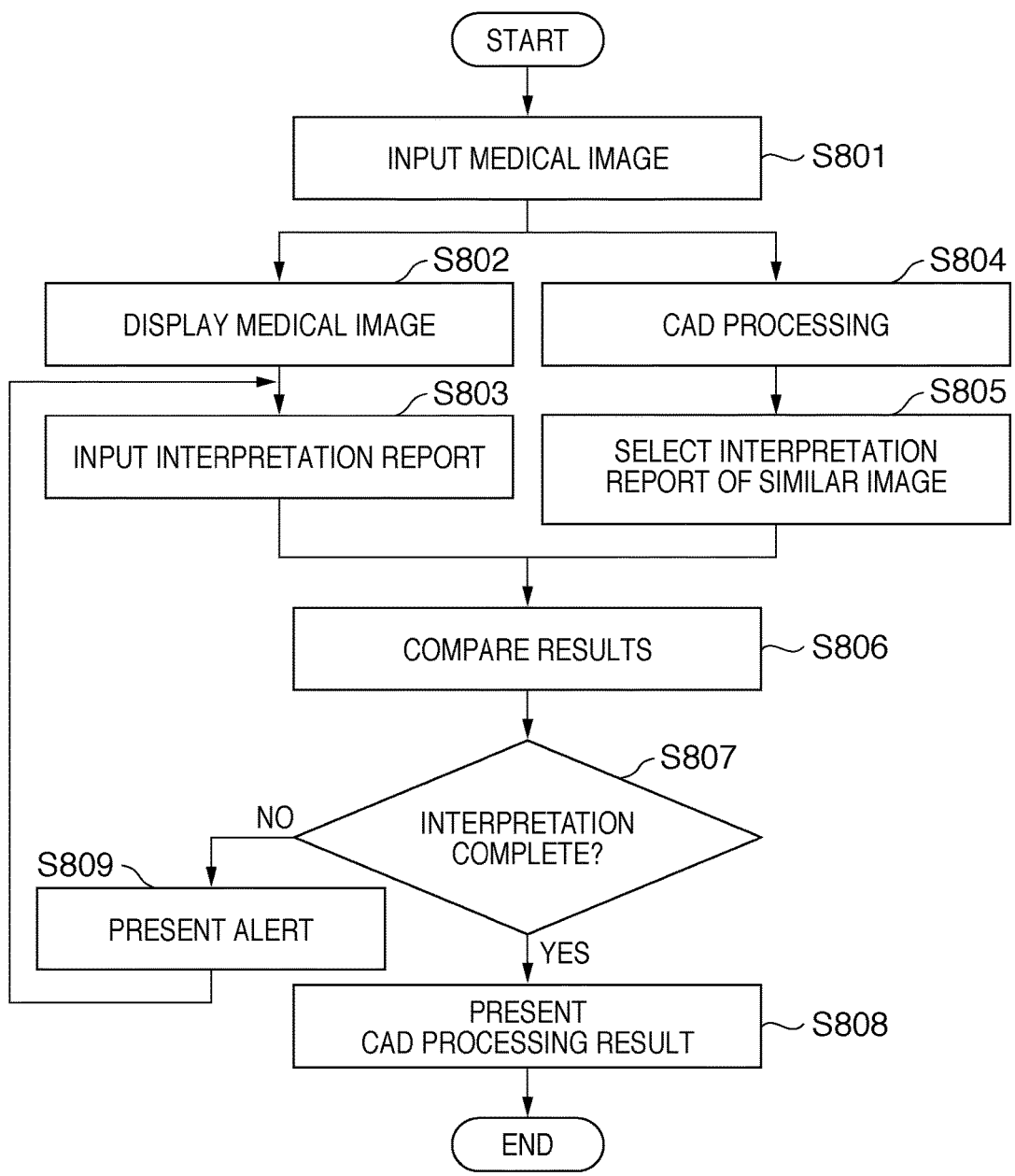
FIG. 8 is a flowchart showing the processing sequence of the medical diagnosis support apparatus 1 according to the third embodiment.

How the control unit 10 of the third embodiment controls the medical diagnosis support apparatus 1 will be described below with reference to the flowchart shown in FIG. 8.

In step S801, a CPU 100 performs processing to input desired medical image data to the medical diagnosis support apparatus 1 in accordance with inputs from a mouse 105 and keyboard 106 (the input medical image data will be referred to as an image to be interpreted hereinafter). In step S802, the CPU 100 performs processing for displaying the image to be interpreted input to the medical diagnosis support apparatus 1 on a monitor 104. In step S803, the CPU 100 performs processing to input interpretation information created by a doctor as an interpretation report (to be defined as a report α hereinafter) to the medical diagnosis support apparatus 1. Then, the interpretation information as the interpretation result of the image to be interpreted is input to the medical diagnosis support apparatus 1. In step S804, the CPU 100 performs processing for acquiring diagnosis information by applying CAD processing to the image to be interpreted input to the medical diagnosis support apparatus 1. That is, medical diagnosis information is acquired from the image to be interpreted by computer processing. Details of the processes in steps S801 to S804 above are the same as those (steps S201 to S204) of the first embodiment, and a detailed description thereof will not be repeated.

Next, the CPU 100 specifies a previous medical image related to the image to be interpreted from the case image database 108 as the storage unit, and acquires previous interpretation information corresponding to the specified previous medical image from the case report database 109 as the storage unit. In this embodiment, an image that has a highest similarity between images with regard to the image to be interpreted of previous medical images stored in the case image database 108 as the storage unit is specified as the previous medical image related to the image to be interpreted. More specifically, in step S805, the CPU 100 selects an image similar to the image to be interpreted input to the medical diagnosis support apparatus 1 from the case image database 108. Then, the CPU 100 acquires an interpretation report (to be defined as an interpretation report β hereinafter) of the selected similar image from the case report database 109.

Note that the similar image of the image to be interpreted is acquired by the following method.

The CPU 100 extracts feature amounts from the image to be interpreted, and compares them with feature amounts extracted from medical image data in the case image database 108. Then, the CPU 100 selects a case image that is closest to the image to be interpreted on a feature space as a similar image. Note that examples of feature amounts to be extracted from medical images include histogram feature amounts of luminance values in medical images and texture feature amounts such as spatial frequencies.

A degree of matching between descriptions included in the previous interpretation information acquired in step S805 and in the interpretation information input in step S803 is calculated. In this embodiment, in step S806, the CPU 100 compares the contents of the interpretation report α with those of the previous interpretation report β of the previous similar image so as to judge, in consideration of the interpretation contents, whether or not the doctor has completed the interpretation.

As for the interpretation report of the previous case, completion of the interpretation has already been confirmed. Furthermore, of the previous cases, an image similar to the image to be interpreted includes more similar contents of the interpretation findings. Therefore, this embodiment uses the interpretation report β of the previous similar image as a report to be compared so as to judge the contents of the interpretation report α. Upon comparison between the two reports, if the contents of the interpretation report α are similar to those of the interpretation report β, a reliability upon judging completion of the interpretation is high.

Hence, in this embodiment, a degree of matching between all findings included in the interpretation report β and those included in the interpretation report α is calculated, and is defined as a reliability of the interpretation report. This degree of matching is calculated by the same method as that of calculating the degree of matching of findings included in CAD diagnosis information and an interpretation report, described in the modification of the second embodiment.

In step S807, the CPU 100 judges that the interpretation is complete if a reliability R of the interpretation report α is equal to or larger than a predetermined value (to be defined as a threshold $R_{th}$ hereinafter). The process then advances to step S808. In this way, when the degree of matching (reliability R) calculated in step S806 is equal to or larger than the predetermined threshold $R_{th}$, the CPU 100 permits presentation of the diagnosis information acquired by the diagnosis processing in step S804. Conversely, when the reliability R is smaller than the threshold, the CPU 100 judges that the interpretation is incomplete, and the process advances to step S809.

Note that a similarity between the image to be interpreted and similar image can be used as a scale upon judging their finding contents. For example, when a similar image having a high similarity is not found as a result of selection, and an interpretation report of a case with a low similarity is selected as a report to be compared, the contents of the findings between the two reports are not so similar to each other. Therefore, in this embodiment, the threshold $R_{th}$ to be referred to is changed based on the similarity between the specified previous medical image and image to be interpreted. That is, in this embodiment, the similarity between images is defined as S, and is used as a criterion of the threshold $R_{th}$ of the reliability R.

Even when the image to be interpreted and similar image are entirely similar to each other, their findings are not always similar to each other. Therefore, the criterion of the threshold has to be set to be lower than the value S, and is expressed by a constant $d_1$. At this time, the threshold $R_{th}$ is expressed by:

[Mathematical 4]

$$R_{th} = \begin{cases} S - d_1 & (S - d_1 > 0) \\ 0 & (S - d_1 \leq 0) \end{cases} \qquad (4)$$

In this embodiment, for example, the constant $d_1$ is set to be $d_1=0.2$.

In step S808, the CPU 100 presents the CAD diagnosis information obtained in step S804 on the monitor 104, and the process advances to the end of processing. Details of this processing are the same as in the first embodiment, and a description thereof will not be repeated.

In step S809, the CPU 100 presents an alert indicating that the interpretation is incomplete and re-interpretation is required, and the process returns to step S803. Since details of the process in step S809 are the same as in the first embodiment (step S207), a description thereof will not be repeated.

According to the arrangement of the third embodiment described above, the following effects can be obtained.

That is, whether or not the interpretation is complete is judged based on a scale as to how many contents of the interpretation report match those of the interpretation report of a previous image similar to the image to be interpreted. Hence, the judgment based on the interpretation contents can be attained, thus making the doctor follow the correct procedures of the interpretation more reliably.

In particular, when the image to be interpreted includes a morbid portion having an obvious feature, a case corresponding to a very similar image is likely to be selected. In this case, a case is also more likely to be similar. Hence, such similar image can be an effectively used to compare the interpretation contents.

Modification of Third Embodiment

The selection processing of the interpretation report β of an image similar to the image to be interpreted in step S805 may adopt the following mode.

When interpretations in follow-ups are to be covered, previously interpreted medical image data and interpretation reports associated with patients as interpretation targets are stored in the case image database 108 and case report database 109. Therefore, in this case, an image most similar to medical image data to be interpreted is the latest interpreted medical image data associated with a patent as an interpretation target. Therefore, processing for selecting the latest interpreted medical image data associated with a patient as an interpretation target in place of selecting medical image data using feature amounts of an image is performed. Then, an interpretation report corresponding to the selected medical image data is used as the interpretation report β, and is compared with the interpretation report α of the interpretation target. In this way, the latest medical image of previous medical images associated with a patient of the image to be interpreted may be specified from the case image database 108 as a previous medical image.

In follow-ups, findings described in a previous interpretation report have to be described in a format in which how these findings have changed in the next interpretation report. Hence, the reliability of the interpretation report α based on the interpretation report β is very effective to judge whether or not the interpretation is complete. Furthermore, in this case, since omissions of recording of previous records are not permitted in principle in association with the interpretation report β, the threshold $R_{th}$ of the reliability has to be set to be a value as closer to 1 as possible.

Fourth Embodiment

The fourth embodiment will be described below. A medical diagnosis support apparatus of the fourth embodiment adopts the same arrangement as that of the third embodiment. That is, a medical diagnosis support apparatus 1 of the fourth embodiment has a case image database 108 and case report database 109, which store previous medical images and pieces of related previous interpretation information.

Figure 9:
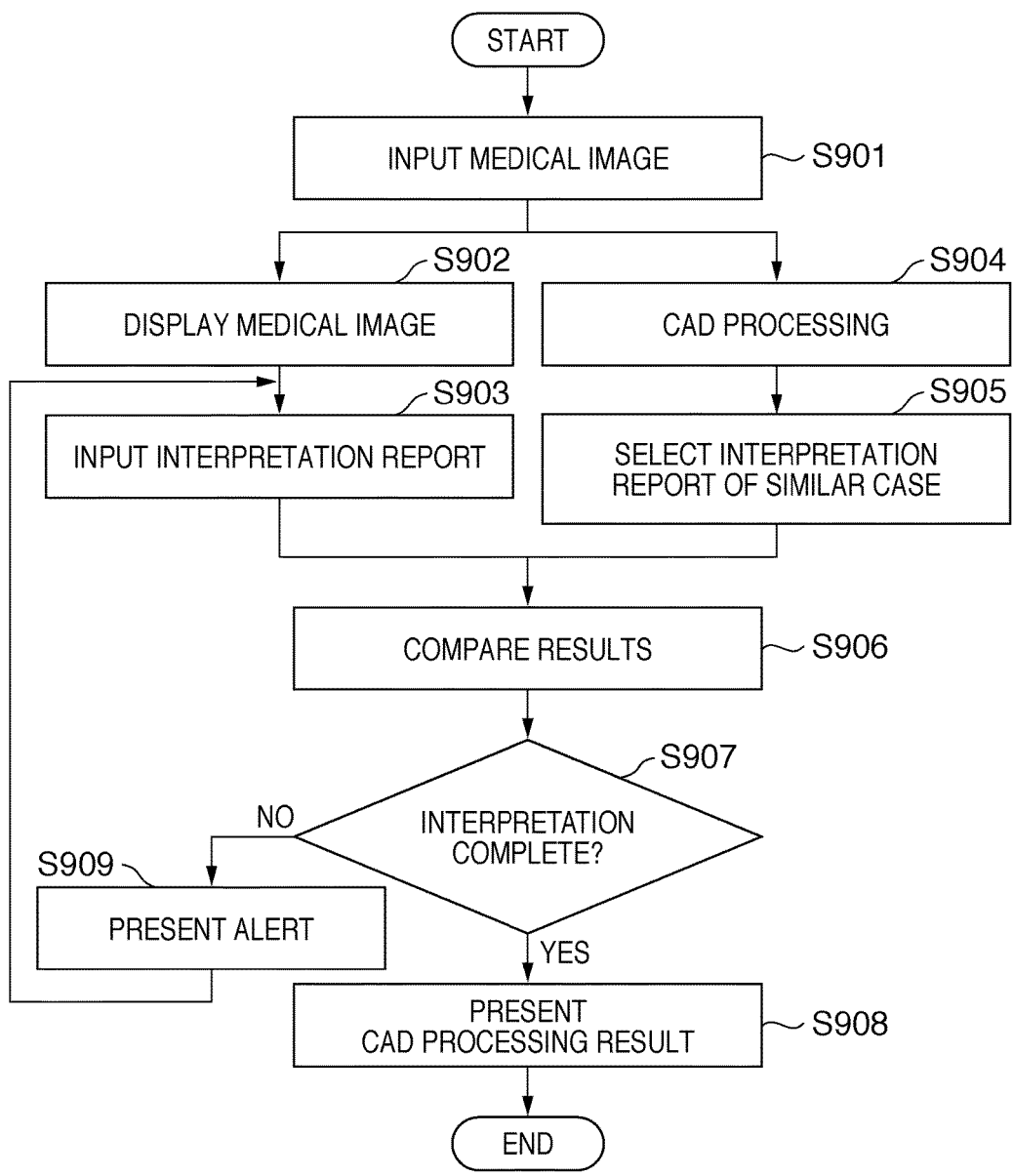
FIG. 9 is a flowchart showing the processing sequence of a medical diagnosis support apparatus 1 according to the fourth embodiment.

How a control unit 10 according to the fourth embodiment controls the medical diagnosis support apparatus 1 will be described below with reference to the flowchart of FIG. 9.

In step S901, a CPU 100 inputs desired medical image data to the medical diagnosis support apparatus 1 in accordance with inputs from a mouse 105 and keyboard 106 (the input medical image data will be referred to as an image to be interpreted hereinafter). In step S902, the CPU 100 performs processing for displaying the image to be interpreted input to the medical diagnosis support apparatus 1 on a monitor 104. In step S903, the CPU 100 inputs interpretation information by a doctor to the medical diagnosis support apparatus 1 as an interpretation report (to be defined as an interpretation report α hereinafter). In step S904, the CPU 100 performs processing for acquiring diagnosis information (to be defined as diagnosis information A hereinafter) of the image to be interpreted by applying CAD processing to the image to be interpreted input to the medical diagnosis support apparatus 1. Since details of the processes in these steps S901 to S904 are the same as those (steps S201 to S204) of the first embodiment, a detailed description thereof will not be repeated.

The CPU 100 specifies a previous medical image related to the image to be interpreted input in step S901 from the case image database 108, and acquires previous interpretation information corresponding to the specified previous medical image from the case report database 109. More specifically, in step S905, the CPU 100 acquires an image whose case itself is similar to the image to be interpreted input to the medical diagnosis support apparatus 1 from the case image database 108. Furthermore, the CPU 100 acquires an interpretation report (to be defined as an interpretation report β hereinafter) of the image of the similar case from the case report database 109. Note that the image of the similar case is acquired by, for example, the following method.

The CAD diagnosis information A for the image to be interpreted and diagnosis information acquired by executing the CAD to images in the case image database 108 are compared to select diagnosis information having a highest degree of matching with the diagnosis information A. The selected diagnosis information will be referred to as diagnosis information B hereinafter. This process is equivalent to specify a previous image corresponding to the diagnosis information B from the case image database 108. At this time, upon comparison between the diagnosis information A and the CAD diagnosis information acquired from previous cases, a degree of matching of findings included in diagnosis information of a certain case with respect to all findings included in the diagnosis information A is calculated and is defined as a degree of matching with the diagnosis information A. Since this degree of matching is calculated by the same method as that of calculating a degree of matching of findings included in the CAD diagnosis information and interpretation report in the modification of the second embodiment, a description thereof will not be repeated. Note that a previous medical image related to the image to be interpreted may be specified by the method described in the second embodiment and the modification of the second embodiment.

In step S906, the CPU 100 compares four pieces of information, that is, the interpretation report α obtained in step S903, the CAD diagnosis information A obtained in step S904, and the diagnosis information B and interpretation report β obtained in step S905, as shown in FIG. 13. Furthermore, the CPU 100 calculates two reliabilities, that is, those of the interpretation reports α and β.

At this time, the CPU 100 calculates a degree of matching the interpretation report α based on the diagnosis information A and that of the interpretation report β based on the diagnosis information B by the same calculation method as that described in the second embodiment or its modification, and these degrees of matching are respectively defined as $C_{\alpha A}$ and $C_{\beta B}$. Furthermore, the CPU 100 sets a reliability $R_A$ of the interpretation report α to be $R_A = C_{\alpha A}$ as in the second embodiment or its modification. Also, the CPU 100 sets a reliability $R_B$ of the interpretation report β of the similar case to be $R_B = C_{\beta B}$.

In step S907, the CPU 100 judges that the interpretation is complete if the value of the reliability $R_A$ of the interpretation report α is equal to or larger than a predetermined value (to be defined as a threshold $R_{th}$ hereinafter), and the process advances to step S908. Conversely, the CPU 100 judges that the interpretation is incomplete if the reliability is smaller than the threshold, and the process advances to step S909.

The detection difficulty varies depending on finding types actually included in the image to be interpreted, and this results in a different CAD accuracy, thus influencing the reliability value. At this time, since the previous similar case includes finding contents similar to the image to be interpreted, the CAD may generate diagnosis information with an equivalent accuracy. Furthermore, the interpretation of the previous similar case is complete. Hence, using the reliability based on the CAD diagnosis information in this case in a threshold, a criterion according to the CAD accuracy with respect to the image to be interpreted at that time can be set. Therefore, this embodiment calculates a degree of matching (reliability $R_B$) between the diagnosis information (B) obtained by processing the specified previous medical image by diagnosis processing means and the acquired previous interpretation information (β), and changes the threshold $R_{th}$ based on the calculated degree of matching. More specifically, the threshold $R_{th}$ used to judge the reliability $R_A$ of the interpretation report α, completion of the interpretation of which has not been confirmed yet, is expressed using the reliability $R_B$ of the interpretation report β, completion of the interpretation of which has already been confirmed. However, since the CAD accuracy for the image to be interpreted does not always perfectly match that for the image of the similar case, a low threshold has to be set by estimating their errors. When this value is expressed as a constant $d_2$, the threshold $R_{th}$ is given by:

[Mathematical 5]

$$R_{th} = \begin{cases} R_B - d_2 & (R_B - d_2 \geq 0) \\ 0 & (R_B - d_2 < 0) \end{cases} \quad (5)$$

In this embodiment, for example, the constant $d_2$ is set to be $d_2 = 0.2$.

In step S908, the CPU 100 presents the CAD diagnosis information A obtained in step S904 on the monitor 104, and the process advances to the end of processing.

In step S909, the CPU 100 presents an alert indicating that the interpretation is incomplete and re-interpretation is required, and the process returns to step S903.

According to the arrangement of the fourth embodiment described above, the following effects can be obtained.

That is, according to the fourth embodiment, the reliability of the interpretation report based on the CAD diagnosis information of the image to be interpreted is judged with reference to that of the interpretation report based on the CAD diagnosis information in the similar case. For this reason, the judgment based on the interpretation contents can be attained, thus making the doctor follow the correct procedures of the interpretation more reliably.

Especially, whether or not the interpretation is complete can be judged according to the CAD accuracy with respect to the image to be interpreted at that time.

Furthermore, in the following case, this embodiment produces a large effect.

When the number of abnormal findings included in the image to be interpreted is very small, the reliability of the interpretation report is either extremely good or bad, and is largely influenced by the CAD accuracy. At this time, two patterns that have different meanings of diagnosis results but assume similar reliability values may be generated as follows unless the CAD accuracy is 100%.

For example, when the image to be interpreted does not include any abnormality at all, and the interpretation doctor has thoroughly interpreted that image, the interpretation report does not include any abnormal finding, but the CAD unwantedly detects false positives and diagnosis information includes abnormal findings (pattern 1).

Conversely, when the image to be interpreted includes an apparent abnormality, but the interpretation doctor has not thoroughly interpreted that image, the interpretation report does not include any abnormal finding, but the CAD diagnosis information includes abnormal findings (pattern 2).

In both the cases, since the interpretation report and CAD diagnosis information do not include any common portions, the reliability $R_A$ assumes a value close to zero. By contrast, according to the fourth embodiment, since the threshold $R_{th}$ of the reliability includes the reliability $R_B$ in the previous similar case, the $R_{th}$ value suited to each pattern can be set.

In case of pattern 1, since the similar case does not actually include any abnormal finding and the CAD is more likely to detect false positives, $R_B$ similarly assumes a value close to zero, and the threshold $R_{th}$ also assumes a value close to zero. In case of pattern 2, since the similar case is more likely to actually include abnormal findings, and the interpreted interpretation report is considered to also describe abnormal findings, $R_B$ assumes a high value, and the threshold $R_{th}$ also assumes a high value.

Therefore, in this embodiment, even when the number of abnormal findings included in the image to be interpreted is small, whether or not the interpretation is complete can be judged appropriately.

Other Embodiments

The embodiments have been explained in detail. The present invention can adopt embodiments in the form of, for example, a system, apparatus, method, program, or storage medium. More specifically, the present invention may be applied to either a system configured by a plurality of devices or an apparatus consisting of a single device.

Note that the present invention includes a case in which the functions of the embodiments are achieved when a software program is directly or remotely supplied to a system or apparatus, and a computer of that system or apparatus reads out and executes the supplied program code.

The program to be supplied in this case is a computer program corresponding to each illustrated flowchart in the embodiments.

Therefore, the program code itself installed in a computer to implement the functional processing of the present invention using the computer implements the present invention. Put differently, the present invention includes the computer program itself for implementing the functional processing of the present invention.

In this case, the form of program is not particularly limited, and an object code, a program to be executed by an interpreter, and script data to be supplied to an OS may be used as long as they have the functions of the program.

As a computer-readable storage medium for supplying the computer program, the following media can be used. For example, a Floppy® disk, hard disk, optical disk, magneto-optical disk, MO, CD-ROM, CD-R, CD-RW, magnetic tape, nonvolatile memory card, ROM, and DVD (DVD-ROM, DVD-R) can be used.

As another program supply method, the user establishes connection to a homepage on the Internet using a browser on a client computer, and downloads the computer program of the present invention from the homepage onto a recording medium such as a hard disk. In this case, the program to be downloaded may be a compressed file including an automatic installation function. Also, program codes that form the program of the present invention may be divided into a plurality of files, which may be downloaded from different homepages. That is, the present invention includes a WWW server that makes a plurality of users download program files required to implement the functional processing of the present invention by the computer.

Also, a storage medium such as a CD-ROM, which stores the encrypted program of the present invention, may be delivered to the user. In this case, the user who has cleared a predetermined condition may be allowed to download key information used to decrypt the encrypted program from a homepage via the Internet. The user executes the encrypted program using the key information to install the program on a computer.

The functions of the aforementioned embodiments can be implemented when the computer executes the readout program. Furthermore, the functions of the aforementioned embodiments may be implemented in cooperation with an OS or the like running on the computer based on an instruction of that program. In this case, the OS or the like executes some or all of actual processes, which implement the functions of the aforementioned embodiments.

Furthermore, some or all of the functions of the aforementioned embodiments may be implemented when the program read out from the storage medium is written in a memory equipped on a function expansion board or a function expansion unit, which is inserted in or connected to the computer. In this case, after the program is written in the function expansion board or unit, a CPU equipped on the function expansion board or unit executes some or all of actual processes based on an instruction of that program.

The present invention is not limited to the aforementioned embodiments, and various changes and modifications can be made without departing from the spirit and scope of the present invention. Therefore, to apprise the public of the scope of the present invention, the following claims are appended.

This application claims the benefit of Japanese Patent Application No. 2007-256009, filed Sep. 28, 2007, which is hereby incorporated by reference herein in its entirety.

The invention claimed is:

1. A medical diagnosis support apparatus comprising:
at least one processor; and
at least one memory storing instructions which, when executed by the at least one processor, cause the apparatus to:
   acquire medical diagnosis information from an image to be interpreted by computer processing;
   receive from a user interpretation information as an interpretation result of the image to be interpreted;
   calculate a degree of matching between the acquired diagnosis information and the interpretation information; and
   permit, when the calculated degree of matching exceeds a predetermined threshold, presentation of the acquired diagnosis information,
   wherein presentation of the acquired diagnosis information is inhibited when the calculated degree of matching does not exceed the predetermined threshold.

2. The medical diagnosis support apparatus according to claim 1, wherein the instructions, when executed by the at least one processor, further cause the apparatus to calculate the degree of matching based on:
   a result obtained by comparing the number of findings included in the interpretation information and the number of findings included in the acquired diagnosis information, and
   a result obtained by determining a degree of ease of detection based on description contents of each of the findings included in the acquired diagnosis information, and comparing the number of findings included in the interpretation information and the number of findings included in the acquired diagnosis information in association with the findings, each of which has the degree of ease of detection larger than a predetermined value.

3. The medical diagnosis support apparatus according to claim 1, further comprising:
   a storage unit configured to store previous medical images and pieces of related previous interpretation information;
   wherein the instructions, when executed by the at least one processor, further cause the apparatus to:
   specify a previous medical image related to the image to be interpreted from the storage unit, and acquire previous interpretation information corresponding to the specified previous medical image from the storage unit; and
   change the threshold based on a degree of matching between diagnosis information obtained by processing the specified previous medical image and the acquired previous interpretation information, the degree of matching being calculated.

4. The apparatus according to claim 1, wherein the instructions, when executed by the at least one processor, further cause the apparatus to inhibit display of the acquired diagnosis information when the calculated degree of matching does not exceed the predetermined threshold.

5. A medical diagnosis support apparatus comprising:
   a storage unit configured to store previous medical images and pieces of related previous interpretation information;
   at least one processor; and
   at least one memory storing instructions which, when executed by the at least one processor, cause the apparatus to:

acquire medical diagnosis information from an image to be interpreted by computer processing;

receive from a user interpretation information as an interpretation result of the image to be interpreted;

specify a previous medical image related to the image to be interpreted from the storage unit, and acquire previous interpretation information corresponding to the specified previous medical image from the storage unit; and determine, based on a comparison between the acquired previous interpretation information and the received interpretation information, whether to permit or inhibit presentation of the acquired diagnosis information.

6. The medical diagnosis support apparatus according to claim 5, wherein the instructions, when executed by the at least one processor, further cause the apparatus to specify an image having a highest similarity between images to the image to be interpreted of the previous medical images stored in the storage unit, as the previous medical image related to the image to be interpreted.

7. The medical diagnosis support apparatus according to claim 6, wherein the instructions, when executed by the at least one processor, further cause the apparatus to:

change a threshold based on a similarity between the specified previous medical image and the image to be interpreted;

calculate a degree of matching between descriptions included in the acquired previous interpretation information and the interpretation information received from the user;

permit, when the calculated degree of matching exceeds a predetermined threshold, presentation of the acquired diagnosis information; and inhibit presentation of the acquired diagnosis information when the calculated degree of matching does not exceed the predetermined threshold.

8. The apparatus according to claim 7, wherein the instructions, when executed by the at least one processor, further cause the apparatus to inhibit display of the acquired diagnosis information when the calculated degree of matching does not exceed the predetermined threshold.

9. A method of controlling a medical diagnosis support apparatus, comprising:

acquiring medical diagnosis information from an image to be interpreted by computer processing;

receiving from a user interpretation information as an interpretation result of the image to be interpreted;

calculating a degree of matching between the acquired diagnosis information and the interpretation information; and permitting presentation of the acquired diagnosis information when the calculated degree of matching exceeds a predetermined threshold, wherein presentation of the acquired diagnosis information is inhibited when the calculated degree of matching does not exceed the predetermined threshold.

10. A method of controlling a medical diagnosis support apparatus, which comprises a storage unit configured to store previous medical images and pieces of related previous interpretation information, comprising:

acquiring medical diagnosis information from an image to be interpreted by computer processing;

receiving from a user interpretation information as an interpretation result of the image to be interpreted;

specifying a previous medical image related to the image to be interpreted from the storage unit, and acquiring previous interpretation information corresponding to the specified previous medical image from the storage unit; and determining, based on a comparison between the acquired previous interpretation information and the received interpretation information, whether to permit or inhibit presentation of the acquired diagnosis information.

11. A non-transitory computer-readable storage medium storing a program for making a computer execute a method of controlling a medical diagnosis support apparatus, the method comprising:

acquiring medical diagnosis information from an image to be interpreted by computer processing;

receiving from a user interpretation information as an interpretation result of the image to be interpreted;

calculating a degree of matching between the acquired diagnosis information and the interpretation information; and permitting presentation of the acquired diagnosis information when the calculated degree of matching exceeds a predetermined threshold, wherein presentation of the acquired diagnosis information is inhibited when the calculated degree of matching does not exceed the predetermined threshold.

12. A non-transitory computer-readable storage medium storing a program for making a computer execute a method of controlling a medical diagnosis support apparatus, which comprises a storage unit configured to store previous medical images and pieces of related previous interpretation information, the method comprising:

acquiring medical diagnosis information from an image to be interpreted by computer processing;

receiving from a user interpretation information as an interpretation result of the image to be interpreted;

specifying a previous medical image related to the image to be interpreted from the storage unit, and acquiring previous interpretation information corresponding to the specified previous medical image from the storage unit; and determining, based on comparison between the acquired previous interpretation information and the received interpretation information, whether to permit or inhibit presentation of the acquired diagnosis information.

* * * * *